(12) United States Patent
Lee et al.

(10) Patent No.: US 9,486,443 B2
(45) Date of Patent: Nov. 8, 2016

(54) PHARMACEUTICAL COMPOSITION FOR PREVENTING OR TREATING HYPERTRIGLYCERIDEMIA OR HYPERTRIGLYCERIDEMIA-ASSOCIATED DISEASES

(71) Applicant: DAEWOONG PHARMACEUTICAL CO., LTD., Gyeonggi-do (KR)

(72) Inventors: Jong-Wook Lee, Gyeonggi-do (KR); Sang-Ho Lee, Gyeonggi-do (KR); Taek-Joo Lim, Seoul (KR); Eun-Ji Koh, Gyeonggi-do (KR)

(73) Assignee: DAEWOONG PHARMACEUTICAL CO., LTD., Gyeonggi-do (KR)

(*) Notice: Subject to any disclaimer, the term of this patent is extended or adjusted under 35 U.S.C. 154(b) by 22 days.

(21) Appl. No.: 14/361,365

(22) PCT Filed: Nov. 28, 2012

(86) PCT No.: PCT/KR2012/010175
§ 371 (c)(1),
(2) Date: May 29, 2014

(87) PCT Pub. No.: WO2013/081373
PCT Pub. Date: Jun. 6, 2013

(65) Prior Publication Data
US 2014/0336228 A1 Nov. 13, 2014

(30) Foreign Application Priority Data
Nov. 30, 2011 (KR) .................. 10-2011-0126431

(51) Int. Cl.
| | | |
|---|---|---|
| *A61K 31/421* | (2006.01) | |
| *A61K 31/4178* | (2006.01) | |
| *A61K 31/4184* | (2006.01) | |
| *C07D 263/22* | (2006.01) | |
| *A61K 31/216* | (2006.01) | |
| *A61K 31/4422* | (2006.01) | |
| *A61K 45/06* | (2006.01) | |
| *A61K 31/41* | (2006.01) | |

(52) U.S. Cl.
CPC .......... *A61K 31/421* (2013.01); *A61K 31/216* (2013.01); *A61K 31/41* (2013.01); *A61K 31/4178* (2013.01); *A61K 31/4184* (2013.01); *A61K 31/4422* (2013.01); *A61K 45/06* (2013.01); *C07D 263/22* (2013.01)

(58) Field of Classification Search
CPC .............. A61K 31/421; A61K 31/216; A61K 31/4422; A61K 45/06; A61K 31/41; A61K 31/4178; A61K 31/4184; C07D 263/22
See application file for complete search history.

(56) References Cited

U.S. PATENT DOCUMENTS

| | | | |
|---|---|---|---|
| 7,071,210 B2 | 7/2006 | Ruggeri | |
| 7,129,265 B2* | 10/2006 | Mason ................ | A61K 31/401 514/422 |
| 2004/0039018 A1 | 2/2004 | Ruggeri | |
| 2006/0128751 A1 | 6/2006 | Ruggeri | |
| 2006/0148763 A1 | 7/2006 | Friesen et al. | |
| 2008/0242711 A1 | 10/2008 | Tung | |
| 2008/0286354 A1 | 11/2008 | Borody | |
| 2009/0137548 A1 | 5/2009 | Ali et al. | |
| 2010/0099716 A1 | 4/2010 | Ali et al. | |
| 2011/0165239 A1 | 7/2011 | Alani et al. | |

FOREIGN PATENT DOCUMENTS

| | | |
|---|---|---|
| WO | 2004/004777 A1 | 1/2004 |
| WO | 2006/014357 A1 | 2/2006 |

OTHER PUBLICATIONS

R. Corti et al. (Atherosclerosis 190 (2007) 106-113).*
Clinical Trial (https://clinicaltrials.gov/archive/NCT01252953/2011_06_21, accessed Nov. 16, 2015, published Jun. 21, 2011).*
Yoshi et al (Hypertens Res vol. 29, No. 6 (2006)).*
Cullen, "Evidence That Triglycerides Are an Independent Coronary Heart Disease Risk Factor", Am J. Cardiol, vol. 86, pp. 943-949, (2000).
Le et al., "The role of hypertriglyceridemia in atherosclerosis", Current Atherosclerosis Reports, vol. 9, Iss. 2, pp. 110-115, (2007).
Stalenhoef et al., "Association of fasting and nonfasting serum triglycerides with cardiovascular disease and the role of remnant-like lipoproteins and small dense LDL", Current Opinion in Lipidology, vol. 19, pp. 355-361, (2008).
Ahaneku et al., "Lipids, Lipoproteins and Fibrinolytic Parameters During Amlodipine Treatment of Hypertension", Journal of Health Science, 46(6), 455-458, (2000).
Chapman et al., "Cholesteryl ester transfer protein: at the heart of the action of lipid-modulating therapy with statins, fibrates, niacin, and cholesteryl ester transfer protein inhibitors", European Heart Journal (2010), 31, 149-164.
Van der Hoogt et al., "Fenofibrate increases HDL-cholesterol by reducing cholesteryl ester transfer protein expression", J. Lipid Res. 2007, 48: 1763-1771.
The European Examination Report for EP Patent Application No. 12852569.8, mailed Feb. 17, 2016, five pages.

* cited by examiner

*Primary Examiner* — Savitha Rao
*Assistant Examiner* — Angela Brown-Pettigrew
(74) *Attorney, Agent, or Firm* — Vorys, Sater, Seymour & Pease LLP; Mih Suhn Koh

(57) ABSTRACT

The present invention is a method for treating hyperlipidemia comprising (4S,5R)-5-[3,5-bis(trifluoromethyl)phenyl]-3-({2-[4-fluoro-2-methoxy-5-(propan-2-yl)phenyl]-5-(trifluoromethyl)phenyl}methyl)-4-methyl-1,3-oxazolidin-2-one or its pharmaceutically acceptable salt and amlodipine or its pharmaceutically acceptable salt at a synergistic ratio of about 4:1.

5 Claims, No Drawings

PHARMACEUTICAL COMPOSITION FOR PREVENTING OR TREATING HYPERTRIGLYCERIDEMIA OR HYPERTRIGLYCERIDEMIA-ASSOCIATED DISEASES

TECHNICAL FIELD

The present invention relates to a pharmaceutical composition for preventing or treating hypertriglyceridemia or hypertriglyceridemia-associated disease. More specifically, the present invention relates to a pharmaceutical composition for preventing or treating hypertriglyceridemia or hypertriglyceridemia-associated disease comprising (4S,5R)-5-[3,5-bis(trifluoromethyl)phenyl]-3-({2-[4-fluoro-2-methoxy-5-(propan-2-yl)phenyl]-5-(trifluoromethyl)phenyl}methyl)-4-methyl-1,3-oxazolidin-2-one or its pharmaceutically acceptable salt; and a calcium channel blocker or a fibrate as active ingredients.

BACKGROUND ART

Hyperlipidemia involves abnormally elevated levels of any or all lipids and/or lipoproteins in the blood. Hyperlipidemias may be classified according to which types of lipids are elevated, that is hypercholesterolemia, hypertriglyceridemia or both in combined hyperlipidemia. Triglycerides are known as one of the independent risk factors of atherosclerosis. Although the relevancy between hypertriglyceridemia and cardiovascular diseases such as atherosclerosis is not still clear, it has been known that hypertriglyceridemia increases the risk of atherosclerosis (Cullen P. Evidence that triglycerides are an independent coronary heart disease risk factor. *Am J Cardiol* 2000; 86:943-9; Le N A, Walter M F. The role of hypertriglyceridemia in atherosclerosis. *Curr Atheroscler Rep* 2007; 9:110-5; Stalenhoef A F, de Graaf J. Association of fasting and nonfasting serum triglycerides with cardiovascular disease and the role of remnant-like lipoproteins and small dense LDL. *Curr Opin Lipidol* 2008; 19:355-61). And also, it has been reported that pancreatitis occurs in people whose triglyceride levels are above 1000 mg/dl or 12 mmol/l.

Meanwhile, the compound of the following formula 1, whose chemical name is (4S,5R)-5-[3,5-bis(trifluoromethyl)phenyl]-3-({2-[4-fluoro-2-methoxy-5-(propan-2-yl)phenyl]-5-(trifluoromethyl)phenyl}methyl)-4-methyl-1,3-oxazolidin-2-one, has a selective cholesterol ester transfer protein (CETP) inhibiting activity. The compound is being developed as a drug for preventing or treating atherosclerosis (International Patent Publication No. WO 2006/014357).

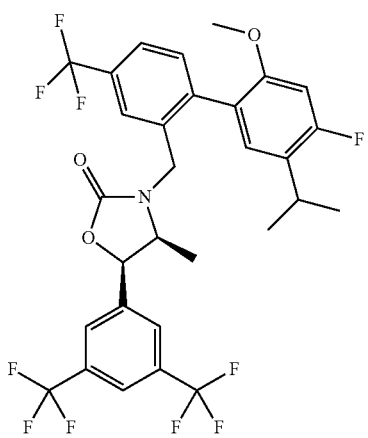

<Formula 1>

DISCLOSURE OF INVENTION

Technical Problem

The present inventors performed various researches for developing a drug or a drug-combination capable of providing effective therapeutic efficacy against hypertriglyceridemia or hypertriglyceridemia-associated disease. Surprisingly, the present inventors found that co-administration of the compound of Formula 1 and a calcium channel blocker or a fibrate can remarkably inhibit the concentration of triglycerides in the blood, in comparison with the administration of the compound of Formula 1 alone.

Therefore, it is an object of the present invention to provide a pharmaceutical composition for preventing or treating hypertriglyceridemia or hypertriglyceridemia-associated disease comprising the compound of Formula 1 and a calcium channel blocker or a fibrate as active ingredients.

Solution to Problem

In accordance with an aspect of the present invention, there is provided a pharmaceutical composition for preventing or treating hypertriglyceridemia or hypertriglyceridemia-associated disease comprising a compound of Formula 1 or its pharmaceutically acceptable salt; and a calcium channel blocker or a fibrate as active ingredients:

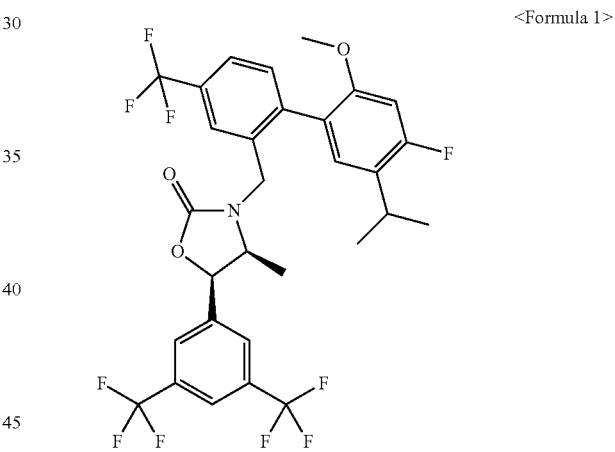

<Formula 1>

In the pharmaceutical composition of the present invention, the calcium channel blocker may be amlodipine or its salt. The fibrate may be fenofibrate or its salt.

The pharmaceutical composition of the present invention may be formulated into a dosage form for oral administration. The dosage form for oral administration may comprise the compound of Formula 1 or its pharmaceutically acceptable salt in an amount suitable for administering in a dose ranging from 10 to 300 mg/day; and/or the calcium channel blocker or the fibrate in an amount suitable for administering in a dose ranging from 5 to 320 mg/day.

Advantageous Effects of Invention

It is newly found by the present invention that co-administration of the compound of Formula 1 and a drug such as amlodipine, fenofibrate, etc. can remarkably inhibit the concentration of triglycerides in the blood, in comparison with the administration of the compound of Formula 1 alone. Therefore, the pharmaceutical composition of the present invention can be usefully applied for preventing or treating hypertriglyceridemia or hypertriglyceridemia-associated diseases.

BEST MODE FOR CARRYING OUT THE INVENTION

The present invention provides a pharmaceutical composition for preventing or treating hypertriglyceridemia or hypertriglyceridemia-associated disease comprising a compound of Formula 1 or its pharmaceutically acceptable salt; and a calcium channel blocker or a fibrate as active ingredients:

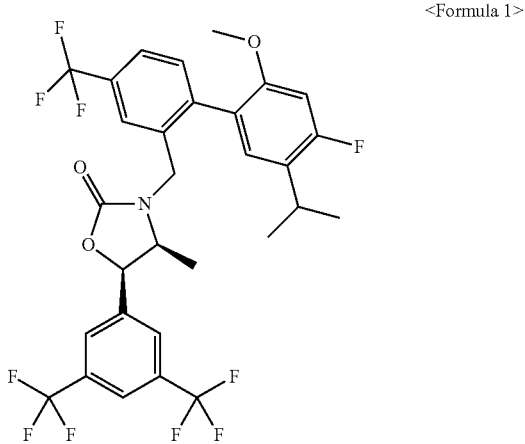 [SMILES: COc1cc(F)c(C(C)C)cc1-c1ccc(C(F)(F)F)cc1CN1C(=O)O[C@H](c2cc(C(F)(F)F)cc(C(F)(F)F)c2)[C@@H]1C]

<Formula 1>

As used herein, the term "hypertriglyceridemia-associated disease" refers to a disease originated from abnormally elevated level of the triglycerides in the blood. The hypertriglyceridemia-associated disease includes combined hyperlipidemia, atherosclerosis, and pancreatitis, but not limited thereto. Examples of the hypertriglyceridemia-associated disease include preferably combined hyperlipidemia and atherosclerosis, more preferably combined hyperlipidemia.

The compound of Formula 1 or its pharmaceutically acceptable salt may be prepared according to the disclosures in the International Publication No. WO 2006/014357. The International Publication No. WO 2006/014357 is incorporated into the present specification as a reference.

The calcium channel blocker (CCB) includes amlodipine or its salt (e.g., besylate, mesylate, nicotinate, camsylate, maleate, adipate, orotate, etc).

The "fibrate" refers to a 2-phenoxy-2-methylpropanoic acid derivative or its pharmaceutically acceptable salt, as defined in US2008/0286354. The US2008/0286354 is incorporated into the present specification as a reference. Examples of the fibrate include drugs such as fenofibrate, bezafibrate, ciprofibrate, vinifibrate, clinofibrate, clofibrate, pirifibrate, etofibrate; and pharmaceutically acceptable salts thereof, but not limited thereto. The fibrate may be preferably fenofibrate or its pharmaceutically acceptable salt.

The pharmaceutical composition of the present invention may be formulated into oral or parenteral dosage forms, preferably into a dosage form for oral administration. And also, the pharmaceutical composition of the present invention may have a form obtained by formulating the compound of Formula 1 and a calcium channel blocker or a fibrate into a single unit dosage form. Alternatively, the pharmaceutical composition of the present invention may have a form obtained by formulating the compound of Formula 1 and a calcium channel blocker or a fibrate into separate dosage forms and then packaging the resulting dosage forms in a single package unit.

The pharmaceutical composition for oral administration having one or two unit dosage form(s) may include a pharmaceutically acceptable carrier, for example, diluents, disintegrating agents, sweeteners, lubricants, and/or flavoring agents, and can be formulated according to conventional methods into tablets, capsules, powders, granules, suspensions, emulsions, syrups, etc. In the case of tablets for oral administration, carriers such as lactose, corn starch, and lubricating agents, e.g. magnesium stearate, are conventionally used. In the case of capsules for oral administration, lactose and/or dried corn starch can be used as a diluent. When an aqueous suspension is required for oral administration, the active ingredient(s) may be combined with emulsifying and/or suspending agents. If desired, certain sweetening and/or flavoring agents may be used. For the pharmaceutical composition for parenteral administration (for example, intramuscular, intraperitoneal, subcutaneous and intravenous administration) having one or two unit dosage form(s), sterile solutions of the active ingredient are usually prepared, and the pH of the solutions should be suitably adjusted and buffered with an isotonic agent and/or a buffering agent.

The compound of Formula 1 or its pharmaceutically acceptable salt contained in the pharmaceutical composition of the present invention may be administered in a therapeutically effective amount ranging from about 10 mg per day to about 300 mg per day to a subject patient. And also, the calcium channel blocker or the fibrate may be administered in a therapeutically effective amount ranging from about 5 mg per day to about 320 mg per day to a subject patient. Of course, the dosages may be changed according to the patient's age, weight, susceptibility, symptom, etc. In an embodiment, the pharmaceutical composition of the present invention may be formulated into a dosage form for oral administration. The dosage form for oral administration may comprise the compound of Formula 1 or its pharmaceutically acceptable salt in an amount suitable for administering in a dose ranging from 10 to 300 mg/day; and/or the calcium channel blocker or the fibrate in an amount suitable for administering in a dose ranging from 5 to 320 mg/day. Of course, the daily dose of the angiotensin II receptor blocker depends on the kinds thereof.

The present invention also provides a use of active ingredients comprising the compound of Formula 1 (i.e., (4S,5R)-5-[3,5-bis(trifluoromethyl)phenyl]-3-({2-[4-fluoro-2-methoxy-5-(propan-2-yl)phenyl]-5-(trifluoromethyl)phenyl}methyl)-4-methyl-1,3-oxazolidin-2-one) or its pharmaceutically acceptable salt; and a calcium channel blocker or a fibrate for the manufacture of a medicament for preventing or treating hypertriglyceridemia or hypertriglyceridemia-associated disease. In the use of the present invention, the hypertriglyceridemia-associated disease includes combined hyperlipidemia, atherosclerosis and pancreatitis, but not limited thereto. Examples of the hypertriglyceridemia-associated disease include preferably combined hyperlipidemia and atherosclerosis, more preferably combined hyperlipidemia. In the use of the present invention, the calcium channel blocker may be preferably amlodipine or its pharmaceutically acceptable salt; and the fibrate may be preferably fenofibrate or its pharmaceutically acceptable salt.

The present invention comprises, within its scope, a method for treating hypertriglyceridemia or hypertriglyceridemia-associated disease in a patient, which comprises administering a therapeutically effective amount of the compound of Formula 1 (i.e., (4S,5R)-5-[3,5-bis(trifluoromethyl)phenyl]-3-({2-[4-fluoro-2-methoxy-5-(propan-2-yl)phenyl]-5-(trifluoromethyl)phenyl}methyl)-4-methyl-1,3-oxazolidin-2-one) or its pharmaceutically acceptable salt; and a therapeutically effective amount of a calcium channel blocker or a fibrate to the patient in need thereof. In the method for treating hypertriglyceridemia or hypertriglyceridemia-associated disease of the present invention, the hypertriglyceridemia-associated disease includes combined hyperlipidemia, atherosclerosis and pancreatitis, but not limited thereto. Examples of the hypertriglyceridemia-associated disease include preferably combined hyperlipidemia and atherosclerosis, more preferably combined hyperlipidemia. In the method for treating hypertriglyceridemia or hypertriglyceridemia-associated disease of the present invention, the calcium channel blocker may be preferably amlodipine or its pharmaceutically acceptable salt; and the fibrate may be preferably fenofibrate or its pharmaceutically acceptable salt.

The present invention will be described in further detail with reference to the following examples. These examples are for illustrative purposes only and are not intended to limit the scope of the present invention.

EXAMPLE 1

Evaluation of Triglyceride-Inhibitory Activities in Hypercholesterolemia-Induced Animals (1) Test Method Male New Zealand White rabbits were used as a test animal. All animals, except for the G1 group animals (negative control group, n=4), were fed with an irradiation-sterilized hypercholesterolemia diet, i.e., DYET #620007 (Purina #5321 chow with 1% cholesterol, Dyets, Inc., Bethlehem, Pa. 18017), which was purchased from Central Lab. Animal Inc. In order to induce hypercholesterolemia, the animals were supplied with the diet for more than 8 weeks. After collecting the blood samples from the animals, serum biochemical analyses were performed thereon. Animals having total cholesterol levels of approximately 870 mg/dL were selected as a hypercholesterolemia-induced animal. The test materials were dissolved in saline containing 0.5% carboxymethylcellulose sodium and 1% Tween 80 and then administered directly into the stomach using an oral syringe adapted with a latex catheter, once per day for 4 weeks. The test groups are as in the following Table 1.

TABLE 1

| Group | Animal (numbers) | Dose volume (mL/kg/day) | Test material First material | Test material Second material | Dose (mg/kg/day) First material | Dose (mg/kg/day) Second material |
|---|---|---|---|---|---|---|
| G1 | 4 | 2 | — | — | 0 | 0 |
| G2 | 8 | 2 | — | — | 0 | 0 |
| G3 | 8 | 2 | Compound of Formula 1 | — | 20 | 0 |
| G4 | 8 | 2 | Compound of Formula 1 | Amlodipine | 20 | 5 |
| G5 | 8 | 2 | Compound of Formula 1 | Fenofibrate | 20 | 30 |

The blood samples were collected through the jugular vein, from the animals at the day initiating the hypercholesterolemia diet supply (i.e., before feeding), and from the animals (which were fasted for 12 to 16 hours before collecting the blood) at 2 weeks and at 4 weeks after initiating the administration of the test material(s).

(2) Results

The triglyceride concentrations in the hypercholesterolemia-induced animals as in the above are presented in the following Table 2. The values in Table 2 represent average triglyceride concentrations (mg/dL) of the respective group.

TABLE 2

| Group | 0 week | 2 weeks | 4 weeks |
|---|---|---|---|
| G1 | 66.3 | 99.5 | 52.5 |
| G2 | 192.6 | 315.1 | 544.1 |
| G3 | 167.4 | 255.8 | 356.7 |
| G4 | 97.9 | 159.1 | 172.1 |
| G5 | 164.6 | 170.4 | 209.0 |

As shown in Table 2, when the compound of Formula 1 and/or amlodipine or fenofibrate were orally administered repeatedly for 4 weeks, the co-administration groups (G4 and G5) showed remarkably high triglyceride-inhibitory activities, in comparison with the group administered with the compound of Formula 1 alone (G3, 356.7 mg/dL at the 4 weeks after initiating the administration). Therefore, it is expected that the combination of the compound of Formula 1 and the calcium channel blocker or the fibrate such as amlodipine or fenofibrate can be usefully applied for preventing or treating hypertriglyceridemia or hypertriglyceridemia-associated diseases.

EXAMPLE 2

Evaluation of Triglyceride-Inhibitory Activities in Hypertriglyceridemia and Hypercholesterolemia-Induced Animals (1) Test Method Male New Zealand White rabbits were used as a test animal. All animals, except for the G1 group animals (negative control group), were fed with an irradiation-sterilized hypertriglyceridemia and hypercholesterolemia diet, i.e., DYET #621082 (Purina #5321 chow with 0.5% cholesterol, 14% coconut oil & 2% Maltose Dextrin, Dyets, Inc., Bethlehem, Pa. 18017), which was purchased from Saeronbio Inc. In order to induce hypertriglyceridemia and hypercholesterolemia, the animals were supplied with the diet for more than 4 weeks. After collecting the blood samples from the animals, serum biochemical analyses were performed thereon. Animals showing significant changes in total cholesterol levels and triglyceride levels were selected, in comparison with the non-treated control group. The selected animals were divided into 4 groups on the basis of the total cholesterol levels and triglyceride levels, thereby all the groups having substantially equal average values in the total cholesterol levels and triglyceride levels. The test materials were dissolved in saline containing 0.5% carboxymethyl-cellulose sodium and 1% Tween 80 and then administered directly into the stomach using an oral syringe adapted with a latex catheter, once per day for 4 weeks. The test groups are as in the following Table 3.

TABLE 3

| Group | Dose volume (mL/kg/day) | Test material | | Dose (mg/kg/day) | |
| | | First material | Second material | First material | Second material |
|---|---|---|---|---|---|
| G1 | 2 | — | — | 0 | 0 |
| G2 | 2 | — | — | 0 | 0 |
| G3 | 2 | Compound of Formula 1 | — | 20 | 0 |
| G4 | 2 | — | Amlodipine | 0 | 5 |
| G5 | 2 | Compound of Formula 1 | Amlodipine | 20 | 5 |

The blood samples were collected through the jugular vein, from the animals at the day initiating the administration of the test material(s) (i.e., at the time of group-dividing, 0 week), and from the animals (which were fasted for 12 to 16 hours before collecting the blood) at 4 weeks after initiating the administration of the test material(s) (n=4-7).

(2) Results

The triglyceride concentrations in the hypertriglyceridemia and hypercholesterolemia-induced animals as in the above are presented in the following Table 4. The values in Table 4 represent average triglyceride concentrations (mg/dL) of the respective group.

TABLE 4

| Group | 4 weeks | Percent inhibition of triglyceride in the blood (%) |
|---|---|---|
| G1 | 35.7 | — |
| G2 | 326.5 | — |
| G3 | 293.1 | 10.2 |
| G4 | 268.0 | 17.9 |
| G5 | 218.5 | 33.1 | shown in Table 4, when the compound of Formula 1 and/or amlodipine were orally administered repeatedly for 4 weeks, the groups administered with the compound of Formula 1 alone (G3) or amlodipine alone (G4) respectively showed 10.2% and 17.9% inhibitions in the triglyceride levels, in comparison with the G2 group. However, the co-administration groups (G5) showed 33.1% inhibition in the triglyceride level in comparison with the G2 group. The triglyceride-inhibitory activity (i.e., 33.1% inhibition) of G5 was more potent in comparison with the sum of triglyceride-inhibitory activities of G3 and G4 (i.e., 28.1% inhibition).

Therefore, it can be acknowledged that the combination of the compound of Formula 1 and the calcium channel blocker such as amlodipine provides synergistic effect in inhibiting triglyceride levels.

The invention claimed is:

1. A method for treating hypertriglyceridemia or a hypertriglyceridemia-associated disease in a patient, which comprises administering a therapeutically effective amount of a compound of Formula 1 or its pharmaceutically acceptable salt in combination with a therapeutically effective amount of amlodipine or its pharmaceutically acceptable salt to the patient in need thereof, wherein the combination is synergistic in treating the hypertriglyceridemia or hypertriglyceridemia-associated disease, and the weight ratio of the amount of the compound of Formula 1 or its pharmaceutically acceptable salt to the amount of amlodipine or its pharmaceutically acceptable salt is about 4:1:

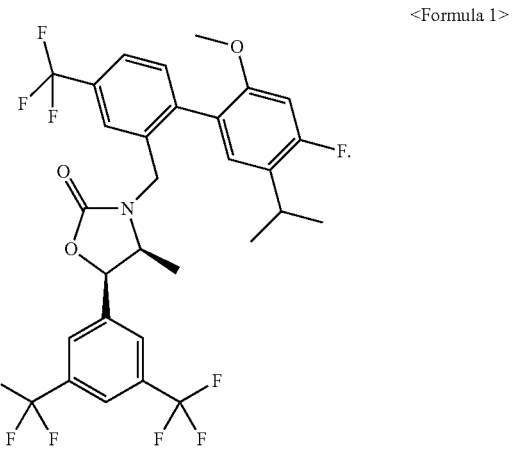

<Formula 1>

2. The method according to claim 1, wherein the compound of Formula 1 or its pharmaceutically acceptable salt in combination with amlodipine or its pharmaceutically acceptable salt are formulated into a dosage form for oral administration.

3. The method according to claim 2, wherein the dosage form for oral administration comprises the compound of Formula 1 or its pharmaceutically acceptable salt in an amount suitable for administering in a dose ranging from 10 to 300 mg/day.

4. The method according to claim 2, wherein the dosage form for oral administration comprises amlodipine or its pharmaceutically acceptable salt in an amount suitable for administering in a dose ranging from 5 to 320 mg/day.

5. The method according to claim 1, wherein the hypertriglyceridemia-associated disease is combined hyperlipidemia, atherosclerosis, or pancreatitis.

* * * * *